US 6,534,674 B2

(12) United States Patent
Kim et al.

(10) Patent No.: US 6,534,674 B2
(45) Date of Patent: Mar. 18, 2003

(54) CRYSTALLINE DISODIUM PAMIDRONATE HYDRATE AND PROCESS FOR PREPARING IT

(75) Inventors: Jae-shin Kim, Seoul (KR); You-Sup Chung, Suwon (KR)

(73) Assignee: Hanlim Pharm. Co., Ltd., Seoul (KR)

( * ) Notice: Subject to any disclaimer, the term of this patent is extended or adjusted under 35 U.S.C. 154(b) by 0 days.

(21) Appl. No.: 09/831,791
(22) PCT Filed: Dec. 9, 2000
(86) PCT No.: PCT/KR00/01434
§ 371 (c)(1),
(2), (4) Date: May 14, 2001
(87) PCT Pub. No.: WO01/42134
PCT Pub. Date: Jun. 14, 2001

(65) Prior Publication Data
US 2002/0193627 A1 Dec. 19, 2002

(30) Foreign Application Priority Data

Dec. 10, 1999 (KR) .............................. 99-56724
Jul. 4, 2000 (KR) .............................. 00-38051

(51) Int. Cl.$^7$ .............................................. C01B 25/45
(52) U.S. Cl. ...................................................... 562/13
(58) Field of Search ........................................ 562/13

(56) References Cited
U.S. PATENT DOCUMENTS 4,711,880 A * 12/1987 Stahl et al. ................. 514/108
5,296,475 A * 3/1994 Fleasch et al. ............. 514/108

* cited by examiner

Primary Examiner—Joseph K. McKane
Assistant Examiner—Andrea D. Small
(74) Attorney, Agent, or Firm—Frommer Lawrence & Haug LLP

(57) ABSTRACT

The present invention relates to a novel crystalline disodium pamidronate 3~4 hydrate and a process for preparing it. More particularly, crystalline disodium pamidronate 3~4 hydrate of the following formula I having the water content of 17.0~20.0 wt % and being in the state of the mixture of trihydrate and tetrahydrate is prepared by neutralizing pamidronic acid with sodium compound, drying the formed disodium pamidronate, dissolving the disodium pamidronate in water, filtering sparingly soluble materials, allowing the filtrate to stand with stirring at normal temperature to form crystals, cooling and filtering the mixture to obtain crystals, and drying at the temperature of 75~85° C. under normal pressure.

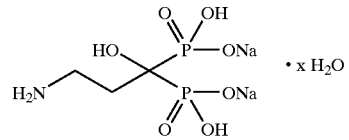

wherein x represents 3 or 4.

The novel disodium pamidronate 3~4 hydrate according to the present invention is much more stable compound structurally than the known disodium pamidronate pentahydrate. When the compound is in storage or is used as pharmaceutical formulations, validity time can be prolonged and it can be formulated as convenient oral preparations such as soft capsule in addition to injections.

1 Claim, 3 Drawing Sheets

Fig. 1b

```
                        PEAKS FILE LISTING
                        ------------------
DATA FILE:    Z05056.PKS         COLLECTED ON 02 FEB 00 AT 13:23:57
SAMPLE IDENTIFICATION:           4
START 2THETA:    5.000           STOP 2THETA:     50.000
STEP SIZE:       0.012           SCAN SPEED:       3.000
COUNTING TIME:   2.000
PEAKS FOUND ON:                  02-FEB-00 AT 14:52:19
                     PEAK FINDING PARAMETERS
                     -----------------------
          THRESHOLD VALUES:           0.0, 0.0
   RELATIVE CUTOFF INTENSITY:         0.0
TYPICAL FULL WIDTH-HALF MAXIMUM:      0.00
MINIMUM FULL WIDTH-HALF MAXIMUM:      0.00
       PEAK   2-THETA    D-SPACE    I(REL)    I(CPS)    FWHM 1     7.548    11.7127      8.73     256.8    0.373
         2     8.304    10.6483     10.31     303.1    0.218
         3    11.288     7.8388    100.00    2941.3    0.161
         4    13.065     6.7762     42.15    1239.8    0.164
         5    15.131     5.8556     11.33     333.3    0.259
         6    15.557     5.6960     13.65     401.4    0.307
         7    16.676     5.3164     44.48    1308.3    0.154
         8    16.957     5.2289     17.44     512.8    0.283
         9    18.542     4.7853      7.85     231.0    0.320
        10    18.938     4.6862      6.30     185.4    0.006
        11    19.292     4.6010      8.06     236.9    0.108
        12    19.969     4.4465      4.25     124.9    0.797
        13    20.456     4.3417     10.06     295.9    0.216
        14    21.436     4.1455      6.12     180.0    0.365
        15    21.783     4.0802      4.74     139.3    0.168
        16    22.197     4.0050      4.66     137.0    7.658
        17    22.731     3.9120     18.63     547.8    0.224
        18    23.130     3.8455     16.43     483.4    0.180
        19    24.346     3.6561     20.74     610.0    0.182
        20    25.152     3.5407      6.13     180.4    0.189
        21    25.625     3.4764      9.90     291.3    0.199
        22    26.351     3.3823      4.24     124.7    0.519
        23    27.709     3.2195      7.13     209.6    0.911
        24    28.113     3.1742      6.73     198.1    0.517
        25    28.663     3.1145     22.48     661.3    0.261
        26    29.940     2.9845     15.17     446.2    0.414
        27    30.184     2.9609     23.24     683.7    1.067
        28    30.574     2.9241     19.27     566.9    0.006
        29    30.770     2.9059     15.89     467.2    0.336
        30    31.066     2.8789     26.22     771.1    0.284
        31    31.476     2.8423     14.62     430.0    0.239
        32    32.040     2.7935     10.78     317.0    0.508
        33    32.392     2.7640     23.51     691.4    0.470
        34    32.586     2.7480     21.78     640.6    0.282
        35    33.125     2.7044      8.17     240.2    0.476
        36    33.749     2.6559      9.12     268.2    1.393
        37    34.434     2.6046     19.00     558.9    0.344
        38    35.158     2.5526      7.41     218.1    0.006
        39    35.951     2.4981      6.37     187.5    0.492
        40    36.261     2.4774      6.66     196.0    1.069
        41    36.735     2.4465     10.59     311.5    0.244
        42    37.816     2.3790     13.91     409.2    0.251
        43    39.300     2.2926      7.49     220.3    0.287
        44    39.490     2.2820      8.35     245.6    0.498
        45    40.211     2.2427     12.04     354.0    0.276
        46    40.801     2.2116      6.45     189.6    1.926
        47    41.645     2.1688      5.46     160.5    2.266
        48    42.191     2.1419      6.48     190.7    0.481
        49    42.813     2.1123      6.09     179.3    0.601
        50    43.380     2.0860      9.96     292.8    0.680
        51    43.895     2.0626      4.92     144.8    0.294
        52    44.397     2.0405      6.77     199.1    0.816
        53    44.862     2.0204      5.01     147.4    0.006
        54    45.086     2.0109      4.78     140.6    0.006
        55    45.257     2.0037      4.41     129.8    0.006
        56    46.013     1.9725      4.29     126.1    4.223
        57    46.610     1.9486      4.98     146.3    0.006
        58    48.037     1.8940      4.18     122.8    0.006
        59    48.843     1.8646      4.79     140.8    1.981
        60    49.861     1.8289      4.39     129.1    0.800
         #  -  peak FWHM is less than step width
```

CRYSTALLINE DISODIUM PAMIDRONATE HYDRATE AND PROCESS FOR PREPARING IT

This application is a 371 of PCT/KR00/01434 Dec. 9, 2000.

FIELD OF INVENTION

The present invention relates to a novel crystalline disodium pamidronate hydrate and a process for preparing it. More particularly, the present invention relates to the novel crystalline disodium pamidronate 3~4 hydrate. The present crystalline disodium pamidronate 3~4 hydrate can be obtained by the following procedures: Disodium pamidronate is obtained after neutralizing pamidronic acid (3-amino-1-hydroxypropane-1,1-diphosphonate) in a solvent with sodium hydroxide and by drying the product which is filtered from reaction mixture. The disodium salt is dissolved in water insoluble material is filtered and the filtrate is allowed to stand with stirring in room temperature to form crystals. This present invention is concerned about the synthetic method of the crystalline disodium pamidronate hydrate, by drying the crystals at the temperature of 75~85° C. and at normal pressure including hydrate percentage of 17.0~20.0 and represented by the following formula I exists in the form of mixture of 3 hydrate and 4 hydrate.

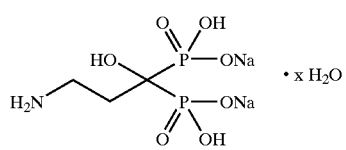

Formula I wherein x is 3 or 4.

BACKGROUND ART

Pamidronic acid and its salt are known compounds and have activities against skeleton symptoms and arthritis symptoms, when orally administered. Various studies have been being carried out on the preparation of the compounds. In particular, there are reports that according to the descriptions of pamidronic acid or disodium salt prepared finally, the stabilites of proceedings for the preparation comprising them and of storage are become different greatly.

Prior Arts are as followed about the synthetic method of disodium pamidronate.

Argentine Patent No. 200,473 disclosed 2 steps of procedures is consist that the proceedings of reacting β-alanine with phosphorus compound(for example, phosphorus acid, phosphorus trichloride, phosphorus oxychloride) to obtain pamidronic acid and that the proceedings of by neutralizing an obtained pamidronic acid with sodium hydroxide, cooling the reaction mixture, or by adding water, methanol, ethanol or acetone to obtain the precipitates in the reaction mixture, besides German Patent Laid-open Publication No. 2,443,963 disclosed the precedures of obtaining sodium salt by completely neutralizing or partially neutralizing pamidronic acid with sodium hydroxide to obtain salt thereof.

However, it has been known that by common neutralizing methods disodium pamidronate was obtained in a hygroscopic form lacking in crystallinity. Thus, non-crystalline materials, which absorb water in various amounts by the action of environmental humidity, are produced. In practice, it has been found that when disodium pamidronate is produced under various conditions for neutralization and working-up procedures, several different solid forms may be produced as identified according to the analysis of X-ray diffraction pattern or IR spectrum.

In case of the salt compounds in the form of multi-hydrates, there are some problems that it is extremely difficult to formulate into preparations suitable for oral administration and further more, to be decreased the stability during storage.

Meanwhile. U.S. Pat. No. 4,711,880 (corresponding to Korean Patent Publication No. 94-817) discloses the process for preparing crystalline disodium pamidronate wherein the crystals obtained from an aqueous solution of disodium pamidronate or a reaction solution of neutralization of pamidronic acid with sodium hydroxide are dried either at room temperature or at somewhat elevated temperature. In the above patent, although it is described that the formation of crystals is initiated at over 50° C. and the drying procedure is carried out at room temperature or somewhat elevated temperature to obtain disodium pamidronate containing water of crystallization and having a good storage stability, the basic inventive concept is regarded merely as utilizing the method of the above mentioned Argentine Pat. No. 200,473. In addition, it has been described that the crystals prepared according to the process of U.S. Pat. No. 4,711,880 has the water content from 24.1 to 24.5 wt % approximately, which corresponds to about 5 moles of water per one mole of disodium pamidronate molecule, to be obtained in the form of a pentahydrate as identified by crystallography.

However, although such disodium pamidronate pentahydrate guarantees a certain degree of stability, it does not secure complete stability as yet and thus, can be used only as injectable formulations. Therefore, its use as common oral formulations such as capsules is practically difficult.

DISCLOSURE OF INVENTION

Thus, the present inventors have tried to establish the means capable for preparing disodium pamidronate hydrate which have a better storage stability and are easy to be formulated into pharmaceutical preparations.

As a result, we have found that the crystal of hydrate in the more stable state, as compared with the prior crystals, can be obtained by a process which comprises neutralizing pamidronic acid with a sodium compound under a certain reaction condition to obtain disodium pamidronate, filtering off the impurities, dissolving the resulting salt in water, allowing the resulting solution to stand at room temperature to induce the crystallization and then drying the resulting crystals at about 80° C. to obtain the crystals of disodium pamidronate hydrate including a low water content of 17.0 to 20.0 wt %, and this invention is accomplished.

Therefore, the purpose of the present invention is to provide the crystalline disodium pamidronate hydrate having a water content of 17.0 to 20.0 wt % in the form of the mixture of crystals of trihydrate and tetrahydrate of disodium pamidronate in view of crystallography and a process for preparation thereof.

The present invention provides disodium pamidronate hydrate as characterized by a crystalline disodium pamidronate hydrate having water content of 17.0–20.0 wt % in the form of the mixture of crystals of trihydrate and tetrahydrate of disodium pamidronate in view of crystallography.

Disodium pamidronate hydrate according to the present invention has the water content different from that in the prior art. The process for preparation of such disodium pamidronate hydrate can be generally divided into the two groups consisting of a method utilizing sodium hydroxide and a method utilizing an organic sodium compound, as follows.

In the process for preparing crystalline disodium pamidronate from the reaction solution for neutralization of pamidronic acid with sodium hydroxide according to the first method, it is characterized to be included the process which pamidronic acid is neutralized with sodium hydroxide at about 90° C. in the range of pH 7.5~8.5: the insoluble materials produced after neutralization is filtered: an alcohol is added to the filtrate to produce a salt: the resulting salt is dissolved in water and is allowed to stand at room temperature to induce crystallization: the resulting crystallizing solution is cooled to obtain the crystals: and then the resulting crystals are dried at the temperature of 75~85° C. under normal pressure to obtain the crystalline disodium pamidronate hydrate.

In the process for preparing crystalline disodium pamidronate from the reaction solution of neutralization of pamidronic acid with an organic sodium compound according to the second method, it is characterized to be included the process which pamidronic acid is neutralized with sodium methoxide or sodium ethoxide in absolute methanol or absolute ethanol under refluxing: the salt produced from neutralization is dissolved in water and the insoluble materials produced are filtered: the filtrate is allowed to stand at room temperature to induce crystallization: the resulting solution is slowly cooled and filtered to obtain the crystals: and then the resulting crystals are dried at temperature of 75~85° C. under normal pressure to obtain the crystalline disodium pamidronate hydrate.

BRIEF DESCRIPTION OF DRAWINGS

FIG. 1b illustrates numerical values of the data corresponding to FIG. 1a, and

DETAILED DESCRIPTION OF INVENTION

Figure 1A:
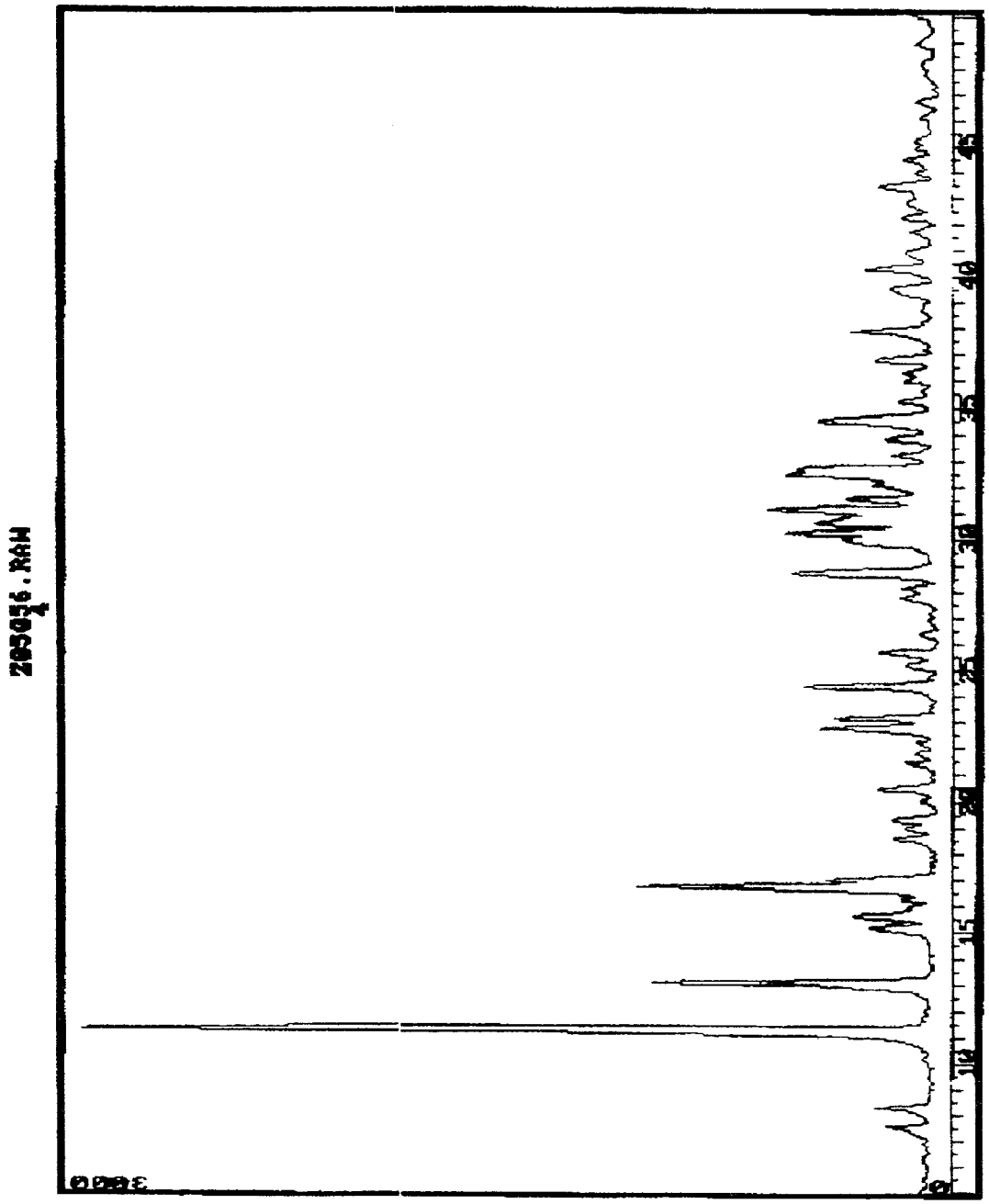
FIG. 1a illustrates the results of the lattice spacings(d-values) and relative line intensities of X-ray diffraction patterns for 3~4 hydrate prepared in the example 2.

If the present invention mentioned above is explained more in detail, as followed.

In the present invention, the superior targeted product having an improved stability and formulation property as compared to the product described in the prior art is prepared by utilizing the process for preparing crystalline disodium pamidronate hydrate, wherein a series of procedures including the step of neutralizing pamidronic acid and sodium compound, the step of forming and filtering the salt, the step of crystallization, the step of obtaining the crystals and the step of drying the product, which the present product is specifically designed so as to be suited for the purpose of the present invention thereby minimizing the water contents improving the stability, and further, is efficiently designed to increase the yield of the desired product. As it was identified that the water content of crystalline disodium pamidronate hydrate prepared according to the process of the present invention is 17.0~20.0 wt %. Disodium pamidronates prepared by methods known in the prior art have the high water content as 5 hydrate as 24% or more, which have problems in that they may be dehydrated at the storage temperature to be above room temperature and it may be impossible to formulate them into oral preparations such as soft capsules. On the contrary to this, the disodium pamidronate 3~4 hydrate having the water content of 17.0~20.0 wt % according to the present invention is a novel and innovative material, which can be solved at once the problems involved in the prior arts as mentioned above. Thus, the present invention includes the process for effectively preparing such an improved hydrate.

The novel disodium pamidronate 3~4 hydrate according to the present invention is prepared in a state of the mixture of trihydrate and tetrahydrate. In the past, it has been known that crystalline disodium pamidronate pentahydrate has better stability than that of its anhydrate or one hydrate to tetrahydrate. On the contrary to the fact known in the prior art as above, the present inventors found out the facts that disodium pamidronate 3~4 hydrate is more stable than pentahydrate as shown in the results of comparative experimental example 1.

According to the methods known in the prior art, it has been known that disodium pamidronate pentahydrate can be obtained by drying at room temperature disodium pamidronate hydrate of which the crystals are produced in an aqueous solution. However, in order to prepare the hydrate having less water content as in the present invention, the conditions for preparation should be differed from those in the prior arts. Specifically, for obtaining the crystals of disodium pamidronate 3~4 hydrate to the present invention, after forming salts, it has been dried at 75~85° C. preferably at about 80° C. for 2 or 3 hours. This means that the salt should be maintained at more elevated temperature as compared to the process for preparing pentahydrate. That means it is that the drying step in the process according to the present invention is to remove unstable and not-combined water molecule in the product so that only water molecules stably combined by hydrogen bond should be existed. In this point, it is an evidence that disodium pamidronate 3~4 hydrate is more stable than pentahydrate. Another proof which the 3~4 hydrate according to the present invention are more stable is explained by structural features characterized in that water molecules in the structure of the compound effectively forming a stable ring structure, which is more stable than the structure of penmtahydrate. Thus, the fact that 3~4 hydrate of crystalline disodium pamidronate is more stable than disodium pamidronate pentahydrate in view of their chemical structures can be comparatively represented as follows:

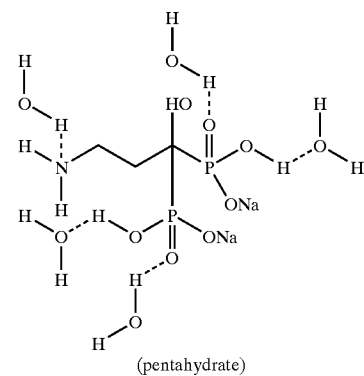

(pentahydrate)

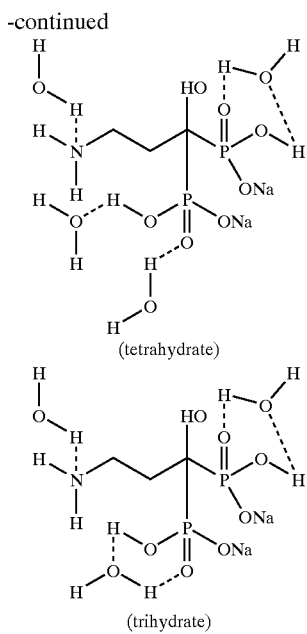

(tetrahydrate)

(trihydrate)

As described above, since crystalline disodium pamidronate 3~4 hydrate prepared by the process according to the present invention has a superior stability to disodium pamidronate pentahydrate, 3~4 hydrate according to the present invention is not change in physical properties including content and water content etc., during a long time storage and therefore, the present 3~4 hydrate can be formulated into the readily available preparations such as soft capsules besides the injectable preparations.

The process according to the present invention is more detailed explained in each steps divided as follows.

First, the step of neutralizing pamidronic acid with sodium hydroxide is carried out in the pH range of 7.5~8.5, preferably 8.1~8.3, and it is for preparing disodium pamidronate and for excluding sodium monohydrogen phosphite and sodium monohydrogen phosphate of reaction impurities. When the neutralization is completed, the insoluble solid product in the reaction solution is filtered off and the filtrate is diluted with an alcohol solvent such as isopropanol and then, cooled to 0° C. below. The resulting solid is dried in an oven maintained at about 90° C. to obtain white disodium pamidronate.

Above mentioned, disodium pamidronate of the result for neutralizing reaction obtained is completely dissolved in hot water about 90° C. Then, the solution is allowed to stand at normal temperature to precipitate the crystals.

In the general method for crystallization of disodium pamidronate conventionally used in the prior art, the solution is heated to about 75° C. and then cooled to 55° C. to obtain the first crop of crystals and then slowly cooled to 20~25° C. to induce further crystallization. However, in such a case a large quantity of solvent is needed due to lower temperature and therefore, the yield is lowered. In addition, since the neutralization is carried out without a precise adjustment of the desired pH level, monosodium or trisodium salts may be produced and sodium monohydrogen phosphite or sodium monohydrogen phosphate, the impurities may be mixed in the final product. Further, due to omit of filtration process the insoluble impurities produced during the reactions are not able to be removed to cause any problem in view of the quality for final product. On the contrary to this, in the present invention the crystallization is carried out with small solvent at high temperature to provide a high yield and the pH level is accurately adjusted so that monosodium or trisodium salts cannot be produced, and sodium mono hydrogen phosphite or sodium mono hydrogen phosphate, the impurities are not mixed in the final product. Therefore, the final product can be maintained in high quality.

Furthermore, the present invention substantially removes the insoluble impurities produced during the reaction by means of filtration procedure so that recrystallization steps can be minimized with times and the purity and quality of the reaction product can be improved. After the precipitated crystals are collected by filtration, they are dried at the temperature of 75~85° C. under atmospheric pressure to prepare the optimized 3~4 hydrate, which is stable even under severe conditions.

Alternatively, the 3~4 hydrate according to the present invention can also be prepared by another method using sodium alkoxide, preferably sodium methoxide or sodium ethoxide, as organic sodium compound which is more advanced method as compared to the method using sodium hydroxide.

In this method, on the contrary to above mentioned method, pamidronic acid is neutralized with sodium methoxide or sodium ethoxide in the presence of absolute methanol or absolute ethanol, wherein the neutralization is carried out at reflux temperature without any pH adjustment. This method uses absolute methanol or absolute ethanol as the solvent in the absence of water and moreover uses sodium methoxide or sodium ethoxide as the organic sodium compound having a good reactivity, so that the quantitative reaction in the ratio of one mole of pamidronic acid to 2 moles of sodium methoxide or ethoxide can be carried out. Particularly, since the reaction is carried out at refluxing temperature, there is no difficulty in controlling the reaction temperature: the pH adjustment is not required for preparation of the salts because the reaction is proceeded in a quantitative manner: and in addition to that, the product is insoluble in methanol or ethanol, it can be obtained in a very high yield. For that reason, the present invention has lots of advantages in view of simple procedures and economical aspect compared to the prior methods.

According to the above two methods of the present invention, crystalline disodium pamidronate can be prepared to contain the water content of 17.0~20.0 wt %, preferably 17.0~18.5 wt %, which corresponds to the mixture of tri- and tetrahydrates. Considering that the water content of 16.2% corresponds to trihydrate and the water content of 20.5% corresponds to tetrahydrate, the water content of 17.0~20.0% obtained according to the present invention represents the water content between trihydrate and tetrahydrate. In view of crystallography, this means that the hydrate of the present invention is prepared in the form of a mixture of trihydrate and tetrahydrate.

As mentioned above, in comparison to pentahydrate prepared according to the prior methods, the 3~4 hydrate according to the present invention is advantageously prepared in high yield and purity by a simple procedure, and particularly, has a superior stability due to markedly lower water content and stable structural characteristics. In practice, it has been identified from the results of comparative stability test, X-ray diffraction pattern analysis and thermal gravimetric analysis that the 3~4 hydrate according to the present invention is more stable than the known pentahydrate. Therefore, the 3~4 hydrate according to the present invention can be formulated into a soft capsule preparation, which was hard to be formulated using the prior pentahydrate, and thus 3~4 hydrate according to the present invention can be prepared in the form of advantageous formulations for oral administration.

The present invention is explained more in detail using examples: however, it is not intended to limit the scope of the present invention.

EXAMPLE 1

Pamidronic acid (50 g) is dissolved in hot sodium hydroxide solution (150 ml) of 12.5% p/v (parts/volume) at 90° C. and the mixture was adjusted to pH 7.5~8.5. By filtering the solution, the insoluble material is removed. The filtrate is added to isopropanol (400 ml) which is stirring. After the mixture is cooled to 0° C. filtered and dried in oven at 90° C. white disodium pamidronate (55.8 g. yield 94%) is obtained.

After the obtained disodium pamidronate is added to hot water (90 ml) about 90° C. dissolved completely, and leaving alone while stirring at normal temperature, crystalized suspension is obtained. After the crystalized suspension is cooled to 0° C. filtered, washed with cold water and dried at 80° C. normal pressure in oven, the crystalline disodium pamidronate (65 g yield 95%) is obtained.

By assaying water content of the obtained crystalline disodium pamidronate with Karlfischer method, the water content is 17.20%.

EXAMPLE 2

23.5 g of pamidronic acid is added to 300 ml of absolute methanol 11.37 g of 95% sodium methoxide is added slowly and the reacture mixture is reacted while refluxing for 12 hours. After the reaction mixture is cooled to 0° C., filtered, and dried in oven at 60° C., 27.5 g of white disodium (3-amino-1-hydroxypropane)bisphosphonate is obtained (yield 97.9%).

After the obtained disodium pamidronate (27.5 g) is added to water (61 ml) and the mixture is heated to 95° C. insoluble material is filtered. By cooling the filtrate gradually to normal temperature, the crystalized suspension is obtained. After the crystalized suspension is cooled to 0° C. stirred for 2 hours at the same temperature, filtered, washed with cold water, the first crop is obtained. After the filtrate is concentrated to 15 ml, cooled below 0° C. and treated by the same method above, the second crop is obtained. After the two crops are combined, and dried at 75° C.~85° C. 31.7 g (yield 92.7%: water content 18.50%) of crystalline disodium pamidronate 3~4 hydrates is obtained.

EXAMPLE 3

23.5 g of pamidronic acid is added to 400 ml of absolute ethanol. 14.18 g of 96% sodium methoxide is added slowly and the reacture mixture is reacted while refluxing for 16 hours. After the reaction mixture is cooled to 0° C., filtered, and dried in oven at 80° C., 28.0 g of white disodium (3-amino-1-hydroxypropane) bisphosphonate is obtained (yield 99.6%).

After the obtained disodium pamidronate (28.0 g) is added to water (62 ml) and the mixture is heated to 95° C., an insoluble material is filtered. By cooling the filtrate gradually to normal temperature, the crystalized suspension is obtained. After the crystalized suspension is cooled to 0° C., stirred for 2 hours at the same temperature, filtered, washed with cold water, the first crop is obtained. After the filtrate is concentrated to 15 ml, cooled below 0° C. and treated by the same method above, the second crop is obtained. After the two crops are combined, and dried at 75° C.~85° C., 32.3 g (yield 94.4%: water content 18.21%) of crystalline disodium pamidronate 3~4 hydrates is obtained.

COMPARATIVE EXAMPLE

The method of example 1 of Korean Patent Publication No. 94-817 (corresponding to U.S. Pat. No. 4,711,880)

74.2 g of substantially anhydrous disodium 3-amino-1-hydroxyropane-1,1-diphosphonate are dissolved while stirring in 500 ml demineralized water heated to 75°. The solution is concentrated slowly under reduced pressure until crystallization begins (This crystallization occurs after approximately 375 ml of water has distilled off.) and the mixture is allowed to cool slowly to room temperature while stirring. After standing overnight, the mixture is stirred for 1 hour in an ice-bath, filtered with suction, washed with a little ice-cold water and dried under approximately 20 mbar at room temperature until the weight is constant. In that manner, disodium 3-amino-1-hydroxypropane-1,1-diphosphonate is obtained in the form of the novel crystal modification containing water of crystallization (Modification E).

This modification is characterized by the lattice distance (d-values) and relative line sensitivities (intensities) of X-ray diffraction pattern for the table 1. The modification has about 24.1~24.5% of water contents and the structure of 5 hydrates.

TABLE 1

| d-values(A) | intensity |
|---|---|
| 10.2 | medium |
| 9.9 | medium |
| 9.2 | very strong |
| 5.91 | very strong |
| 5.57 | strong |
| 5.42 | very strong |
| 5.30 | strong |
| 5.14 | medium |
| 5.02 | very strong |
| 4.97 | very strong |
| 4.63 | very strong |
| 4.41 | strong |
| 4.16 | strong |
| 4.07 | weak |
| 4.04 | medium |
| 3.95 | very strong |
| 3.75 | strong |
| 3.67 | weak |
| 3.63 | medium |
| 3.61 | very weak |
| 3.58 | very weak |
| 3.51 | medium |
| 3.43 | strong |
| 3.38 | medium |
| 3.15 | medium |
| 3.14 | medium |
| 3.09 | medium |
| 3.03 | very strong |
| 3.01 | very strong |
| 2.98 | strong |
| 2.97 | very weak |
| 2.91 | very strong |
| 2.82 | strong |
| 2.80 | medium |
| 2.78 | medium |
| 2.75 | strong |
| 2.73 | weak |
| 2.71 | weak |
| 2.69 | weak |
| 2.67 | medium |
| 2.66 | medium |

TABLE 1-continued

| d-values(A) | intensity |
|---|---|
| 2.63 | strong |
| 2.62 | strong |
| 2.61 | strong |
| 2.58 | very strong |
| 2.57 | very strong |

EXPERIMENTAL EXAMPLE 1

Stability tests on the disodium pamidronate hydrate prepared in the above example 2 were carried out and the test results were listed in the followings.
1. Test materials: (1) anhydrous disodium pamidronate.
   (2) disodium pamidronate 3~4 hydrates prepared in the example 2 (water contents 18.50%).
   (3) disodium pamidronate 5 hydrates (water contents 24.41%)
2. Test methods: (1) 1.000 g~1.200 g of anhydrous disodium pamidronate was accurately weighed and 15 samples were prepared.
   (2) 1.000 g~1.200 g of disodium pamidronate 3~4 hydrates was accurately weighed and 15 samples were prepared.
   (3) 1.000 g~1.200 g of disodium pamidronate 5 hydrates was accurately weighed and 15 samples were prepared.
   (4) The tests were carried out under the following conditions:
      1) Temperature (T) and humidity (relative humidity: RH):
         i) 24° C., 50% RH, ii) 40° C., 0% RH, iii) 40° C., 75% RH
      2) Times:
         i) 1 week, ii) 2 weeks, iii) 3 weeks, iv) 4 weeks, v) 5 weeks
   (5) After the tests were carried out, each sample was dried under reduced pressure (below 5 mmHg) at 150° C. for 5 hours, weighed the lost weight and determined the water contents.

The results of tests listed on the table 2. The values show water contents (%).

TABLE 2

| sample\condition | times | 24° C. 50% RH | 40° C. 0% RH | 40° C. 75% RH |
|---|---|---|---|---|
| anhydrous | 1 week | 1.45 | 0.02 | 7.14 |
|  | 2 weeks | 8.42 | 0.06 | 14.39 |
|  | 3 weeks | 13.34 | 0.05 | 18.20 |
|  | 4 weeks | 17.19 | 0.08 | 18.24 |
|  | 5 weeks | 17.84 | 0.10 | 18.22 |
| 3–4 anhydrous (water contents 18.50%) | 1 week | 18.19 | 17.12 | 17.20 |
|  | 2 weeks | 18.03 | 17.20 | 17.66 |
|  | 3 weeks | 18.04 | 17.37 | 17.45 |
|  | 4 weeks | 18.31 | 17.10 | 17.15 |
|  | 5 weeks | 18.28 | 17.22 | 17.26 |
| 5 anhydrous (water contents 24.41%) | 1 week | 19.14 | 24.44 | 24.02 |
|  | 2 weeks | 18.79 | 24.19 | 24.43 |
|  | 3 weeks | 18.29 | 23.52 | 24.35 |
|  | 4 weeks | 18.43 | 23.01 | 23.65 |
|  | 5 weeks | 18.37 | 22.21 | 23.55 |
| Stability evaluation (Stable hydrate) |  | 3–hydrate | anhydrous form 3–4 hydrate 5 hydrate | 3–4 hydrate 5 hydrate |

As shown in the test results, the water contents of 3~4 hydrates (water contents: 18.50) and 5 hydrates (water contents: 24.42) were maintained stably under the conditions of 40° C., 0)% RH and 40° C., 75% RH. However, in the case of 5 hydrates, a part of the water contents (24.41%) is lost from 1 week under the condition of 24° C., 50% RH and the 5 hydrates becomes to 3~4 hydrates. In the case of anhydrous form, though it is maintained stably under the condition of 24° C., 0% RH, it absorbed water under the condition of 24° C., 50% RH and begins to be converted to monohydrate, dihydrates and finally to 3~4 hydrates after 4 weeks. In the case of the condition of 40° C., 75% RH, it also began to be converted to monohydrate, dihydrates and to 3~4 hydrates after 3 weeks. Accordingly, we knew the facts that in all cases, disodium pamidronate hydrates have the tendencies to be converted to stable 3~4 hydrates and that 3~4 hydrates obtained in the example 2 are structurally the most stable.

EXPERIMENTAL EXAMPLE 2

In order to confirm the physical properties of 3~4 hydrates prepared in the example 2, the lattice distances (d-values) and relative line sensitivities of X-ray diffraction patterns were measured on the conditions of step sizes 0.012 from 2 theta 5 to 2 theta 50, scan velocity 3,000 and time 2,000 by using Rigaku D/Max-IIIB X-ray Diffractometer (XRD). The test results were shown on FIG. 1a and FIG. 1b. Thermal Gravity Assay for 3~4 hydrates (TGA data) was carried out by using TA Instruments Model 2950 TGA Thermal Analyzer (TGA). The lost weight of the 3~4 hydrates was measured by gradually raising the temperature of 10° C. per minute from room temperature to 500° C. The results were shown on FIG. 2.

Figure 2:
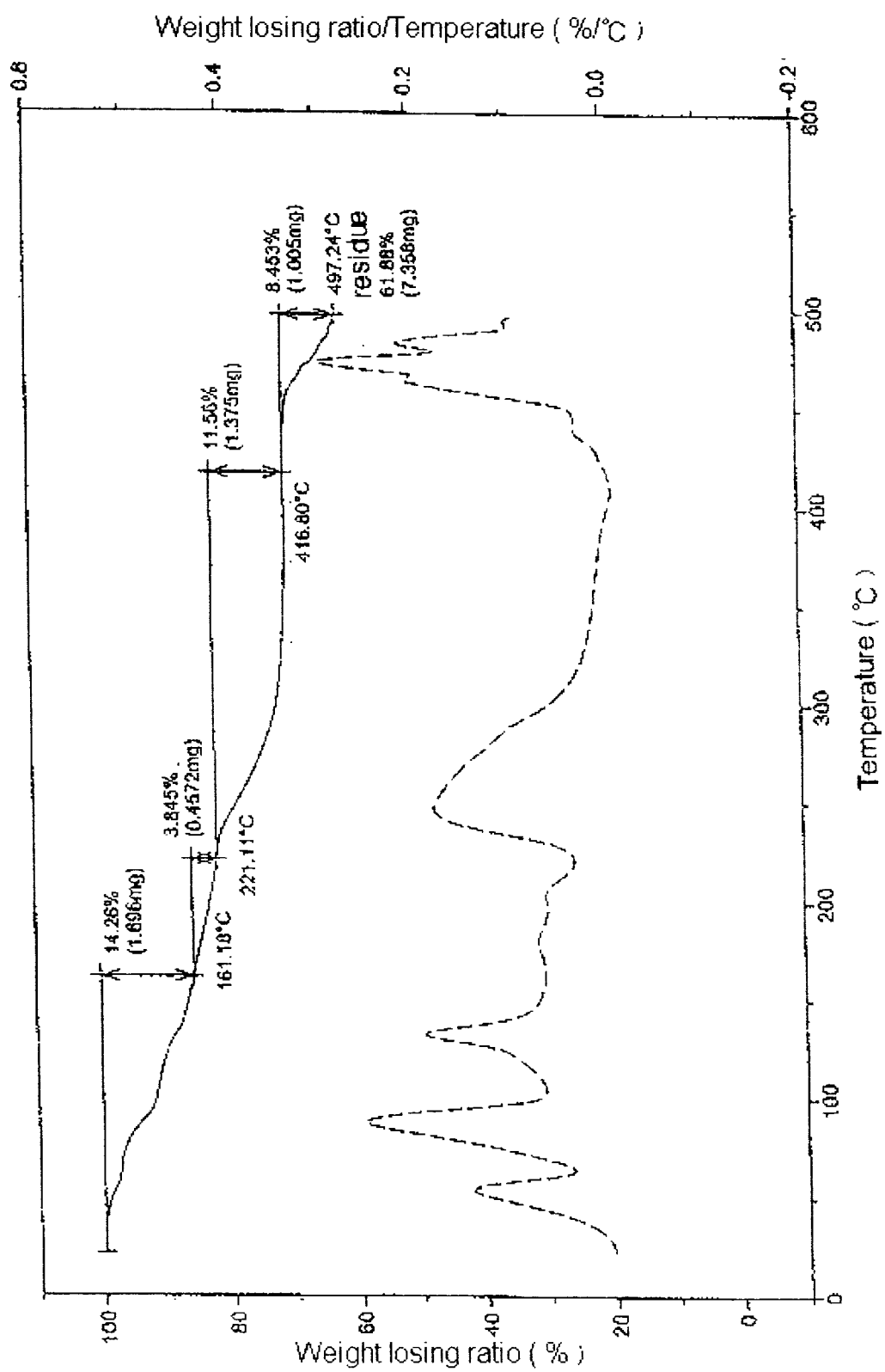
FIG. 2 illustrates a graph showing thermal gravity assay data (TGA data) for 3~4 hydrate prepared in the example 2.

As shown on the FIG. 1a and FIG. 1b. relatively intensive peaks of 3~4 hydrates at 2 theta 11.288, 13.065 and 16.676 could be confirmed. As seen from the results of the FIG. 2. If considering the decomposition temperature of anhydrous disodium pamidronate is 221~228° C. Water loss begins from relatively high temperature of 50° C. which is approved to be stable and the weight loss is 18.105 (14.26%+3.845%, error of measurement ±3%) till 221.11° C. It is showed that the hydrates of the present invention are 3~4 hydrates.

EXPERIMENTAL EXAMPLE 3

Soft gelatine capsules (125 mg) were respectively prepared from the crystalline disodium pamidronates of example 2 and comparative example by a conventional soft capsule manufacturing method. The soft capsules were stored in chamber which is controlled a constant temperature and hymidity (24° C., 50% RH) for 6 months. The stabilities of the soft capsules were tested by visual observation for the changes of properties, colors or shapes. No changes are observed in the case of the samples of example 2. However, the samples of comparative example were changed in shapes (partly collapse by releasing water), colors and dewy phenomena on inner parts of the capsules. Therefore, the hydrates of example 2 were much superior in stabilities to those of comparative example.

As fully stated above, in the present invention, the process for the preparation of disodium pamidronate is carried out with small solvent at high temperature or stable refluxing temperature to provide a high yield. As the neutralization is carried out under specific conditions, monosodium salt or trisodium salt is not produced and sodium monohydrogen phosphite or sodium monohydrogen phosphate is not mixed in the final product. Furthermore, the present invention substantially removes the insoluble impurities produced during the reaction by means of filtration procedure so that recrystallization steps can be minimized and the purity and quality of the reaction product can be improved. Specially, as the formed crystals are dried at the temperature of 75~85° C. under normal pressure, disodium pamidronate hydrate including the water content of 17.0~20.0%) and being in the state of the mixture of trihydrate and tetrahydrate is prepared as crystals. This hydrate corresponds to 3~4 hydrate is more stable crystalline compound structurally than the known pentahydrate. When it is in storage or used as pharmaceutical formulations, the validity time can be prolonged and it can be formulated with convenient oral preparations such as soft capsule besides injections.

What is claimed is:

1. A process for the preparation of crystalline disodium pamidronate 3–4 hydrate having a water content of 17.0–20.0 wt % which has the following lattice spacings (d-values) and relative line intensities (intensities) of its X-ray powder pattern:

| d values (Angstrom) | Intensity | Evaluation |
|---|---|---|
| 11.7 | 256.8 | Weak |
| 10.6 | 303.1 | Weak |
| 7.84 | 2942.3 | Very strong |
| 6.78 | 1239.8 | Very strong |
| 5.86 | 333.3 | Weak |
| 5.70 | 401.4 | Medium |
| 5.32 | 1308.3 | Very strong |
| 5.23 | 512.8 | Medium |
| 4.79 | 231.0 | Weak |
| 4.69 | 185.4 | Very weak |
| 4.60 | 236.9 | Weak |
| 4.45 | 124.9 | Very weak |
| 4.34 | 295.9 | Weak |
| 4.15 | 180.0 | Very weak |
| 4.08 | 139.3 | Very weak |
| 4.00 | 137.0 | Very weak |
| 3.91 | 547.8 | Medium |
| 3.85 | 483.4 | Medium |

-continued

| d values (Angstrom) | Intensity | Evaluation |
|---|---|---|
| 3.66 | 610.0 | Strong |
| 3.54 | 180.4 | Very weak |
| 3.48 | 291.3 | Weak |
| 3.38 | 124.7 | Very weak |
| 3.22 | 209.6 | Weak |
| 3.17 | 198.1 | Weak |
| 3.11 | 661.3 | Strong |
| 2.98 | 446.2 | Medium |
| 2.96 | 683.7 | Strong |
| 2.92 | 566.9 | Strong |
| 2.91 | 467.2 | Medium |
| 2.88 | 771.1 | Strong |
| 2.84 | 430.0 | Medium |
| 2.79 | 317.0 | Weak |
| 2.76 | 691.4 | Strong |
| 2.75 | 640.6 | Strong |
| 2.70 | 240.2 | Weak |
| 2.66 | 268.2 | Weak |
| 2.60 | 558.9 | Strong |
| 2.55 | 218.1 | Weak |

Evaluation: very strong, strong, medium, very weak

Evaluation: very strong, strong, medium, very weak comprising the steps of:
neutralizing pamidronic acid with sodium methoxide or sodium ethoxide in absolute methanol or absolute ethanol at reflux to produce a salt;
dissolving the resulting salt in water;
filtering insoluble materials from the dissolved salt;
allowing the resulting solution to stand at room temperature to form crystals;
cooling the resulting crystalline solution slowly;
filtering the cooled solution to obtain the crystals; and
drying the resulting crystals at a temperature of 75–85° C. under normal pressure to obtain the crystalline disodium pamidronate 3–4 hydrate.

\* \* \* \* \*